United States Patent [19]

Stoll

[11] 4,425,801

[45] Jan. 17, 1984

[54] DEVICE AND PROCEDURE FOR MEASURING IN SITU STRENGTH OF CONCRETE AND THE LIKE

[76] Inventor: Ulrich W. Stoll, 2121 Hall, Ann Arbor, Mich. 48104

[21] Appl. No.: 336,669

[22] Filed: Jan. 4, 1982

[51] Int. Cl.³ .............................................. G01N 3/00
[52] U.S. Cl. ....................................... 73/803; 73/848
[58] Field of Search ................ 73/803, 843, 847, 848, 73/845, 842; 52/698

[56] References Cited

U.S. PATENT DOCUMENTS

| 889,240 | 6/1908 | Kanski ............................ 52/698 X |
| 2,691,293 | 10/1954 | Patterson ......................... 52/698 X |
| 3,605,366 | 9/1971 | Zakim ............................. 52/698 X |

*Primary Examiner*—Jerry W. Myracle
*Attorney, Agent, or Firm*—Stephenson and Boller

[57] ABSTRACT

A device and procedure for measuring the strength of brittle material such as concrete in which a measurable torque is applied to a body member embedded in the material. The body member has a reacting surface which contacts a portion of the material to be tested and exerts a compressive force thereon in response to the application of torque to the body member. A thin layer of compressible material is provided on the body member adjacent the reacting surface to ensure unimpeded localized rupture of the material during the test. Torque is applied to the body member through an elongated rod which has one end secured to the body member and the opposite end extending outwardly from a surface of the material. In a preferred embodiment, the elongated rod is first turned in one direction to break the bond between the material and the device and turned in the opposite direction to apply the compressive force to a portion of the material.

11 Claims, 7 Drawing Figures

DEVICE AND PROCEDURE FOR MEASURING IN SITU STRENGTH OF CONCRETE AND THE LIKE

BACKGROUND OF THE INVENTION

In construction projects utilizing concrete structural members such as cast-in-place reinforced concrete beams or columns in a multi-story structure, it is important to have the capability to measure in situ the compressive strength of particular structural members. In particular, it is often desirable to establish whether a lower limit strength has been achieved in critical members to assure that it is safe to remove temporary supplemental supports and/or impose additional loading during construction. Delaying unnecessarily the removal of support or the adding of such additional loading will lengthen the construction period and correspondingly increase project costs.

A common method for estimating in situ the strength of concrete structural members is the "pull out" test. This test normally calls for an anchor bolt with an appropriately sized transverse flange or extension to be embedded in the concrete before hardening. After the concrete has hardened, the exposed end of the anchor bolt is pulled and the force required to rupture the concrete is measured. A hydraulic jack, screw jack or the like is typically employed to apply the necessary pulling force to the anchor bolt, and necessarily exerts a reacting force against the surface of the concrete structure.

Several limitations and deficiencies in the pull out test have become apparent. First, in order to limit the amount of required pull-out force and to preclude a non-indicative local crushing failure, it is necessary to embed the anchor bolt near the surface of the concrete and the results of the test therefore may not be representative of the overall concrete structure. Second, the pull-out forces tend to impose shear and tensile stresses along the potential rupture surface, whereas the actual stresses imposed on a concrete member under load tend to be shear and compressive. Third, the pull-out forces are generally imposed in a direction transverse to the direction of actual critical forces imposed under load. Fourth, a relatively large force is required to pull out the anchor bolt so that a specially fabricated jacking and force measuring device is needed. Such devices tend to be expensive and prone to maladjustment or damage under adverse field conditions. Fifth, the jacking device requires a smooth, flat and hard bearing surface to react against, thus requiring special precautions during casting and construction. Sixth, the anchor bolt must extend perpendicular to the bearing surface, thus requiring precautions to assure that the bolt is not tipped or dislodged during the pouring and setting of the concrete. Finally, the pull out test may cause a conical piece of material to be broken away at the surface of the structural member which is unsightly and may require repair or filling.

It is the object of the present invention to provide a device and procedure for measuring in situ the compressive strength of concrete structural elements which overcomes and circumvents the various deficiencies and limitations in the prior art.

SUMMARY OF THE INVENTION

The present invention provides a device and procedure for measuring the strength of brittle material such as concrete in which a body member is embedded in the material and a measurable turning force, rather than a pulling force, is applied to the body member. The body member is preferably thin and disk-like, although the invention is not limited to a body member of any particular size or shape. The body member further includes means forming a reacting surface thereon operable to exert a compressive force on a portion of the material to be tested in response to the turning force applied to the body member. The reacting surface may be formed of one or more projections extending outwardly from the body member and secured thereto or integral therewith.

Torque is applied to the body member through an elongated rod, one end of which is secured to the body member, the opposite end extending outwardly from a surface of the material. The rod may be releasably secured to the body member or formed integrally therewith, and is typically embedded in the material prior to hardening. A conventional torque wrench is attached to the free end of the rod and carries a device capable of measuring the magnitude of the torque applied to the body member.

To measure the compressive strength of a concrete member, the torque wrench is manually operated to turn the elongated rod in one direction to break the bond between the hardened material and the surface of the rod. The torque required to break this bond may then be measured. The torque wrench is then operated to turn the elongated rod in the opposite direction so that it engages the body member and exerts a turning force thereon which is translated into a compressive force against a portion of the concrete. The torque is increased until either a value corresponding to the lower limit strength of the material is reached or the concrete ruptures. At this point, the elongated rod may be removed and the resulting void filled if desired.

This invention thus provides an improved device and procedure for measuring the strength of concrete structural elements. Strength can be measured at any desired depth and from any accessible exposed or favored surface. The volume of material disposed during measurement is minimal and does not vary with the depth of the location chosen. The critical stresses imposed on the concrete during the test are shear and compressive stresses, which are analagous to the actual stresses encountered under load, and are in the plane of the critical forces imposed under load. Application of the required torque is accomplished manually, is within the capability of average adults, and does not require contact with the surface of the structural member. Finally, any rupturing of the concrete during the test is completely internal and not visually discernible from the surface, and does not significantly affect the post-measurement strength of the structural member.

Further objects, features and advantages of this invention will become apparent from a consideration of the accompanying description, the appended claims, and the following drawing in which:

FIG. 2 is an enlarged side view of the body member and elongated rod of the present invention;

Figure 1:
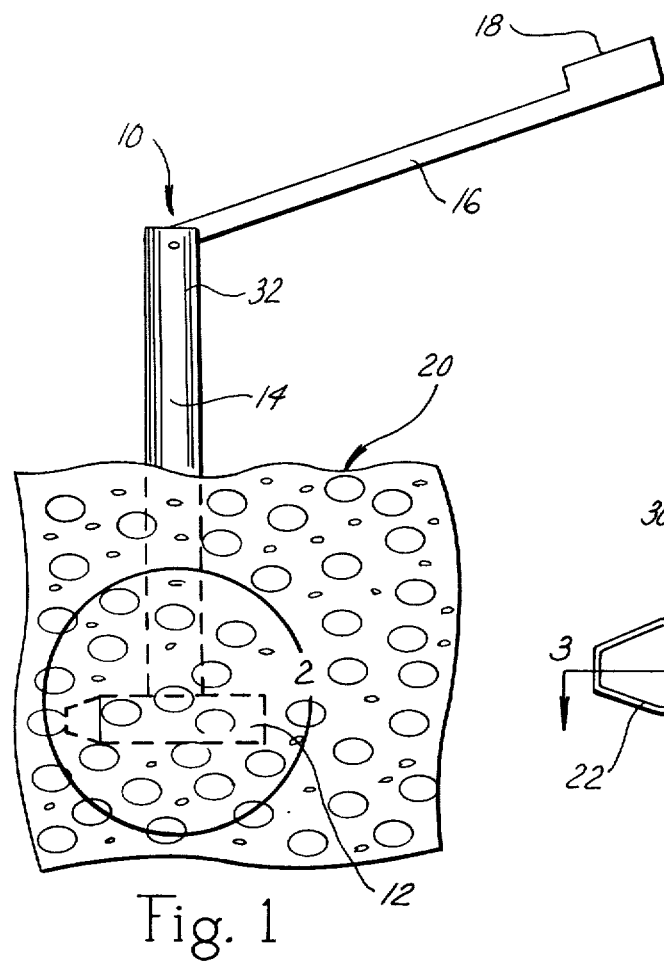
FIG. 1 is a side view of a concrete structural element, broken away to show the measuring device of the present invention operatively associated therewith.

With reference to the drawing, the measuring device of this invention, indicated generally at 10, is shown in FIG. 1 in position to measure the strength of a concrete structural member 20. The device 10 includes a body member 12, an elongated rod 14, and a conventional torque wrench 16 to which a torque measuring device 18 is attached. The strength of the structural member 20 is measured by applying a measured torque to the body member 12, which exerts a compressive force on the concrete, as will appear more fully hereinafter.

Figures 3, 4, 5:
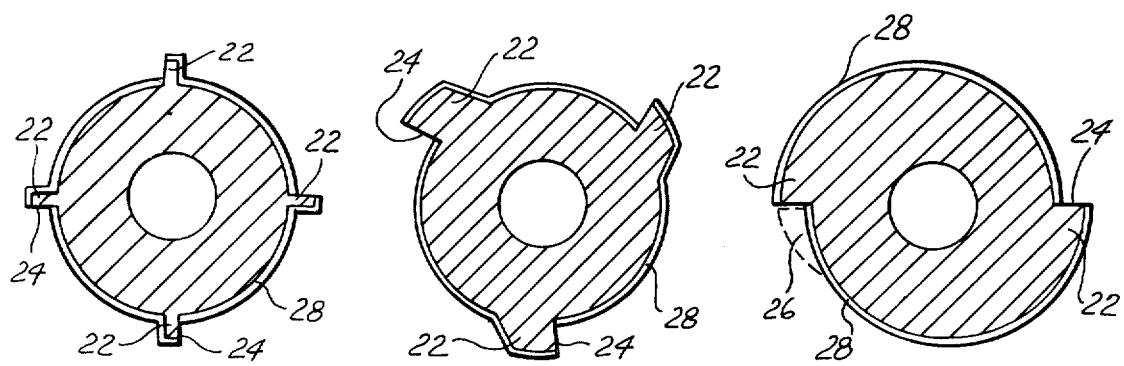
FIGS. 3–5 are top sectional views of the body member of this invention, disclosing alternative forms thereof, as seen from substantially the line 3—3 in FIG. 2.

As seen in FIG. 2, the body member 12 is preferably thin and disklike, although the invention is not limited to a body member of any particular size and shape. One or more projections 22 are provided on the body member 12 and extend substantially radially outwardly therefrom. The projections 22 may be secured to the body member 12 or they may be formed integrally therewith. FIGS. 3-5 show some of the alternative forms the body member 12 may assume. Each projection 22 provides a reacting surface 24 which is in a plane substantially parallel to the axis of rotation of the body member 12, so that upon application of torque to the body member 12, a compressive force is exerted on the concrete in the area of the projections 22.

In testing the strength of structural members, torque is applied to the body member 12 until a value corresponding to the lower limit strength of the material is achieved or until the material ruptures. When rupture occurs, a piece of material in the shape of a convex cusp breaks away, as indicated at 26 in FIG. 3. A compressible zone 28 is provided on the body member 12 into which the convex cusp 26 can move upon rupture. The zone 28 may, for example, comprise a layer of resilient material, such as polyurethane or polyethylene, applied to the body member 12. The layer 28 will yield sufficiently to accomodate the cusp 26 to assure that rupture is unimpeded and readily detectable.

Figure 6:
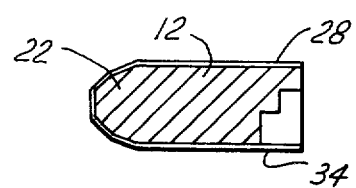
FIGS. 6 and 7 are enlarged side sectional views of the body member of this invention, disclosing alternative forms thereof.
Figure 7:
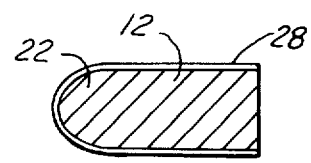

Torque is applied to the body member 12 through the elongated rod 14. The rod 14 has a first end portion 30 which is secured to the body member 12 and an opposite end portion 32 which extends outwardly from a surface of the structural member 20. The torque wrench 16 is secured to the free end 32 of the rod 14. In one embodiment, the rod 14 is releasably secured to the body member 12 so that when the rod 14 is turned in one direction it turns independently of the body member 12, and when it is turned in the opposite direction, it causes the body member 12 to be turned with it. For example, the rod end portion 30 and the body member 12 may be cooperatively threaded (FIG. 2), or the end portion 30 may be provided with a cleat 34 which is engageable with the body member 12 (FIG. 6). In an alternative embodiment, the rod 14 may be fixed to the body member 12 or formed integrally therewith (FIG. 7).

The strength of the structural member 20 is measured as follows. First, the body member 12 and the elongated rod 14 are embedded in the concrete before it hardens. The body member 12 may be embedded at any depth and in any orientation, provided the free end 32 of the rod 14 extends outwardly from any surface of the structural member 20. The surface from which the rod 14 extends need not be smooth, level and planar, nor need it be the top surface of the structural member.

After the concrete has hardened, the torque wrench 16 is attached to the free end 32 of the rod 14 and operated to apply a torque to the rod 14. The amount of torque applied to the rod 14 depends upon the force applied to the end of the torque wrench and the length of the torque wrench. By providing a torque wrench 16 of appropriate length, a large amount of torque can be applied to the rod 14 through a small amount of force on the end of the torque wrench 16. Thus, although a large amount of torque is required in measuring the strength of the material, adults of average size and strength are fully capable of supplying the necessary force.

To exert a compressive force on the concrete, torque tending to turn the rod 14 and the body member 12 in one direction (counterclockwise in FIGS. 3-5) is applied. However, it will normally be preferable to first rotate the rod 14 in the opposite direction to break the bond between the concrete and the rod caused by hardening of the concrete. In embodiments of this invention wherein the rod 14 is integral with the body member 12 or is otherwise not releasably secured thereto, the body member 12 will also be rotated in this direction prior to the exertion of compressive force, and consequently, the bond between the concrete and the body member will first be broken. The torque required to break the bond may be measured and used in calculating the strength of the concrete.

Torque is applied in the direction in which compressive force is exerted on the concrete in increasing magnitude until a value corresponding to the desired lower limit strength of the material is achieved or until the concrete ruptures. In embodiments wherein the rod 14 is releasably secured to the body member 12, the rod 14 is then removed from the concrete, leaving a neat cylindrical hole which can readily be filled if desired. In embodiments wherein the rod 14 is not releasably secured to the body member 12, the rod 14 may be cut off at the surface of the structural member. The procedure of this invention thus ensures that no unsightly defects remain in tested structural members and that the strength of structural members is not affected by the test.

The invention provides an improved device and procedure for measuring in situ the strength of concrete structural members. The device exerts combined compressive and shear forces which correspond more precisely to actual forces encountered by structural members under load than do the forces exerted by conventional devices. The device is easier to use, is usable in more locations and orientations, and has less effect on the strength and appearance of structural members than conventional devices.

What is claimed is:

1. A device for measuring the strength of brittle material such as concrete comprising a body member embedded in said brittle material, said body member comprising a substantially disklike member configured to form at least one generally radially outwardly extending surface forming a reacting surface on said body member operable to exert a compressive force on said brittle material in response to a measurable torque applied to said body member.

2. The device according to claim 1 further including a layer of compressible material on at least a portion of the external surfaces of said body member exclusive of said reacting surface.

3. The device according to claim 2 wherein the radially outer surface of said disklike member extending in one circumferential direction from said reacting surface intersects said reacting surface at the radially inner end thereof, the radially outer surface of said disklike member extending in the opposite direction from said reacting surface intersects said reacting surface at the radially outer end thereof, and said radially outer surface of said disklike member adjacent said reacting surface at the radially inner and outer ends thereof having said layer of compressible material disposed thereon.

4. The device according to claim 1, further including an elongated rod having one end secured to said body member and the other end extending outwardly from a surface of said brittle material and a torque wrench mounted on said elongated rod and operable upon manual manipulation thereof to apply a force to said elongated rod tending to turn said rod and therefore said body member.

5. The device according to claim 4 wherein said elongated rod is releasably secured to said body member.

6. The device according to claim 4 wherein said elongated rod is integral with said body member.

7. A method for measuring the compressive strength of brittle material such as concrete comprising the steps of:
   a. embedding in the material to be tested a body member having a reacting surface,
   b. applying a torque to said body member tending to turn said body member in one direction causing said reacting surface to exert a compressive force on said brittle material, and
   c. measuring said torque.

8. The method according to claim 7, wherein said body member is first rotated in the direction opposite to said one direction.

9. The method according to claim 8, wherein the torque required to rotate said body member in said opposite direction is measured.

10. The method according to claim 7, wherein torque is applied up to a predetermined value corresponding to the required strength of the material.

11. The method according to claim 7, wherein torque of an increasing magnitude is applied until the material ruptures.

* * * * *